(12) United States Patent
Daito et al.

(10) Patent No.: US 9,057,793 B2
(45) Date of Patent: Jun. 16, 2015

(54) FLUID ANALYZER WITH MIRROR AND METHOD OF USING SAME

(71) Applicant: Schlumberger Technology Corporation, Sugar Land, TX (US)

(72) Inventors: Shigeo Daito, Yokohama (JP); Shunsuke Fukagawa, Arlington, MA (US); Shunsuke Yamazaki, Yokohama (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 13/910,002

(22) Filed: Jun. 4, 2013

(65) Prior Publication Data

US 2014/0353481 A1    Dec. 4, 2014

(51) Int. Cl.
*G01V 5/08*    (2006.01)
*G01V 8/10*    (2006.01)

(52) U.S. Cl.
CPC ........................................ *G01V 8/10* (2013.01)

(58) Field of Classification Search
CPC ................................. G01N 21/03; G01V 8/00
USPC ................ 250/256, 266, 269.1, 269.4, 269.6, 250/269.8
See application file for complete search history.

(56) References Cited

U.S. PATENT DOCUMENTS

| | | | |
|---|---|---|---|
| 7,336,356 B2 | 2/2008 | Vannuffelen et al. | |
| 7,458,252 B2 | 12/2008 | Freemark et al. | |
| 7,511,813 B2 | 3/2009 | Vannuffelen et al. | |
| 8,285,491 B2 | 10/2012 | Xie et al. | |
| 2007/0013911 A1* | 1/2007 | Difoggio | 356/436 |
| 2009/0180101 A1 | 7/2009 | Csutak | |
| 2009/0296086 A1 | 12/2009 | Appel et al. | |
| 2011/0061439 A1 | 3/2011 | Dong et al. | |
| 2011/0083842 A1 | 4/2011 | Indo et al. | |
| 2013/0034842 A1* | 2/2013 | Tunheim et al. | 435/3 |

FOREIGN PATENT DOCUMENTS

WO    2009/009409    1/2009

OTHER PUBLICATIONS

Wikipedia about "Beam Splitter" at http://en.wikipedia.org/wiki/Beam_splitter.

(Continued)

*Primary Examiner* — David Porta
*Assistant Examiner* — Meenakshi Sahu
(74) *Attorney, Agent, or Firm* — Daryl R. Wright; Jody DeStefanis (57) ABSTRACT

A fluid analyzer of a downhole tool is provided. The downhole tool is positionable in a wellbore penetrating a subterranean formation. The wellbore has a downhole fluid thereabout. The downhole tool has a housing with a flowline therethrough for receiving the downhole fluid. The fluid analyzer includes at least one optical source to pass a light through an optical window and through the downhole fluid in the flowline, at least one photodetector to measure the light passed through the downhole fluid in the flowline, and at least one optical mirror. An optical path of the light extends from the optical source to the photodetector. An optical path length is defined as a length of a portion of the optical path within the flowline. The optical mirror is positionable about the flowline, and has an optical layer selectively passing the light from the optical mirror to the photodetector whereby the optical path length may be varied.

20 Claims, 9 Drawing Sheets

(56) References Cited

OTHER PUBLICATIONS

International search report and written opinion for the equivalent PCT patent application No. PCT/US2014/040487 issued on Oct. 1, 2014.

\* cited by examiner

FLUID ANALYZER WITH MIRROR AND METHOD OF USING SAME

BACKGROUND

The present disclosure relates generally to wellsite operations. In particular, the present disclosure relates to formation evaluation involving downhole devices, such as fluid analyzers.

Wellbores are drilled to locate and produce hydrocarbons. A downhole drilling tool with a bit at an end thereof is advanced into the ground to form a wellbore. As the drilling tool is advanced, a drilling mud is pumped through the drilling tool and out the drill bit to cool the drilling tool and carry away cuttings. The fluid exits the drill bit and flows back up to the surface for recirculation through the drilling tool. The drilling mud is also used to form a mudcake to line the wellbore.

During the drilling operation, various downhole evaluations may be performed to determine characteristics of the wellbore and surrounding formation. In some cases, the drilling tool may be provided with devices to test and/or sample the surrounding formation and/or fluid contained in reservoirs therein. In some cases, the drilling tool may be removed and a downhole wireline tool may be deployed into the wellbore to test and/or sample the formation. These samples or tests may be used, for example, to determine whether valuable hydrocarbons are present.

Formation evaluation may involve drawing fluid from the formation into the downhole tool for testing and/or sampling. Various devices, such as probes or packers, may be extended from the downhole tool to establish fluid communication with the formation surrounding the wellbore and to draw fluid into the downhole tool. Downhole tools may be provided with fluid analyzers and/or sensors to measure downhole parameters, such as fluid properties. Examples of downhole devices are provided in U.S. Pat. No. 7,458,252, U.S. Pat. No. 7,336,356, U.S. Pat. No. 8,285,491, US2011/0061439, and WO2009/009409, the entire contents of which are hereby incorporated by reference herein.

SUMMARY

In at least one aspect, the present disclosure relates to a fluid analyzer of a downhole tool positionable in a wellbore penetrating a subterranean formation. The wellbore has a downhole fluid thereabout. The downhole tool has a housing with a flowline therethrough for receiving the downhole fluid. The fluid analyzer includes at least one optical source to pass a light through an optical window and through the downhole fluid in the flowline, at least one photodetector to measure the light passed through the downhole fluid in the flowline, and at least one optical mirror. An optical path of the light extends from the optical source to the photodetector. An optical path length is defined as a length of a portion of the optical path within the flowline. The optical mirror is positionable about the flowline, and has an optical layer selectively passing the light from the optical mirror to the at least one photodetector whereby the optical path length may be varied.

In another aspect, the present disclosure relates to a downhole tool positionable in a wellbore penetrating a subterranean formation. The wellbore has a downhole fluid thereabout. The downhole tool includes a housing having a flowline extending therethrough to receive the downhole fluid, and a fluid analyzer. The fluid analyzer includes at least one optical source to pass a light through an optical window and through the downhole fluid in the flowline, at least one photodetector to measure the light passed through the downhole fluid in the flowline, and at least one optical mirror. An optical path of the light extends from the optical source to the photodetector. An optical path length is defined as a length of a portion of the optical path within the flowline. The optical mirror is positionable about the flowline, and has an optical layer selectively passing the light from the optical mirror to the at least one photodetector whereby the optical path length may be varied.

In yet another aspect, the present disclosure relates to a method of measuring fluid of a wellbore penetrating a subterranean formation. The method involves deploying a downhole tool into the wellbore. The downhole tool has a flowline and a fluid analyzer therein. The fluid analyzer includes at least one optical source, at least one photodetector and at least one optical mirror. The method also involves drawing a downhole fluid into the flowline of the downhole tool, and passing light from the optical source through an optical window and through the downhole fluid in the flowline. An optical path of the light extends from the optical source to the photodetector. An optical path length is defined as a length of a portion of the optical path within the flowline. The method further involves varying the optical path length by selectively passing the light from the optical mirror to the photodetector, and measuring the light passed through the downhole fluid in the flowline with the photodetector.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

Embodiments of fluid analyzers with mirror and methods of using same are described with reference to the following figures. The same numbers are used throughout the figures to reference like features and components.

FIGS. 1.1 and 1.2 depict schematic views, partially in cross-section, of a wellsite with a downhole drilling tool and a downhole wireline tool, respectively, deployed into a wellbore for performing downhole formation evaluation in accordance with embodiments of the present disclosure;

FIGS. 3.1 and 3.2 depict schematic views of a linear fluid analyzer with an active mirror in a transmission mode and a reflection mode, respectively, in accordance with an embodiment of the present disclosure;

FIGS. 4.1 and 4.2 depict schematic views of a bent fluid analyzer with an active mirror in a transmission mode and a reflection mode, respectively, in accordance with an embodiment of the present disclosure;

FIGS. 5.1 and 5.2 depict schematic views of an angular fluid analyzer with an active mirror in a transmission mode and a reflection mode, respectively, in accordance with an embodiment of the present disclosure;

FIGS. 6.1 and 6.2 depict schematic views of a multi-bent fluid analyzer with passive half and wavelength selective mirrors, respectively, in accordance with an embodiment of the present disclosure;

FIGS. 7.1-7.3 depict schematic views of a multi-bent fluid analyzer with multiple active mirrors with light passing through first, second and third portions of a flowline, respectively, in accordance with an embodiment of the present disclosure;

DETAILED DESCRIPTION

The description that follows includes exemplary systems, apparatuses, methods, techniques, and instruction sequences that embody techniques of the inventive subject matter. However, it is understood that the described embodiments may be practiced without these specific details.

The present disclosure relates to formation evaluation involving fluid analysis. In particular, the present disclosure describes systems, apparatuses and methods for performing optical fluid analysis. A fluid analyzer is positionable in a downhole tool and deployable into a wellbore for measuring properties of fluid drawn into the downhole tool. The fluid analyzer is configured to permit measurements at a variety of optical path lengths, and/or optimization of a desired optical path length. The fluid analyzer includes a flowline with one or more passive and/or active mirrors to selectively permit the passage of light therethrough and/or to selectively reflect light to another location for measurements. The flowline may be linear or have one or more bends therein with the mirrors placed in desired positions therealong for selectively passing light through the fluid and taking desired measurements.

'Formation evaluation' as used herein relates to the measurement, testing, sampling, and/or other analysis of wellsite materials, such as gases, fluids and/or solids. Such formation evaluation may be performed at a surface and/or downhole location to provide data, such as downhole parameters (e.g., temperature, pressure, permeability, porosity, etc.), material properties (e.g., viscosity, composition, density, etc.), and the like.

'Fluid analysis' as used herein relates to a type of formation evaluation of downhole fluids, such as wellbore, formation, reservoir, and/other fluids located at a wellsite. Fluid analysis may be performed by a fluid analyzer capable of measuring fluid properties, such as viscosity, composition, density, temperature, seismic, pressure, flow rate, optical parameters, etc. Fluid analysis may be performed using, for example, optical sensors (e.g., spectrometers), gauges (e.g., quartz), densitometers, viscometers, resistivity sensors, nuclear sensors, and/or other fluid measurement and/or detection devices.

Figure 11:
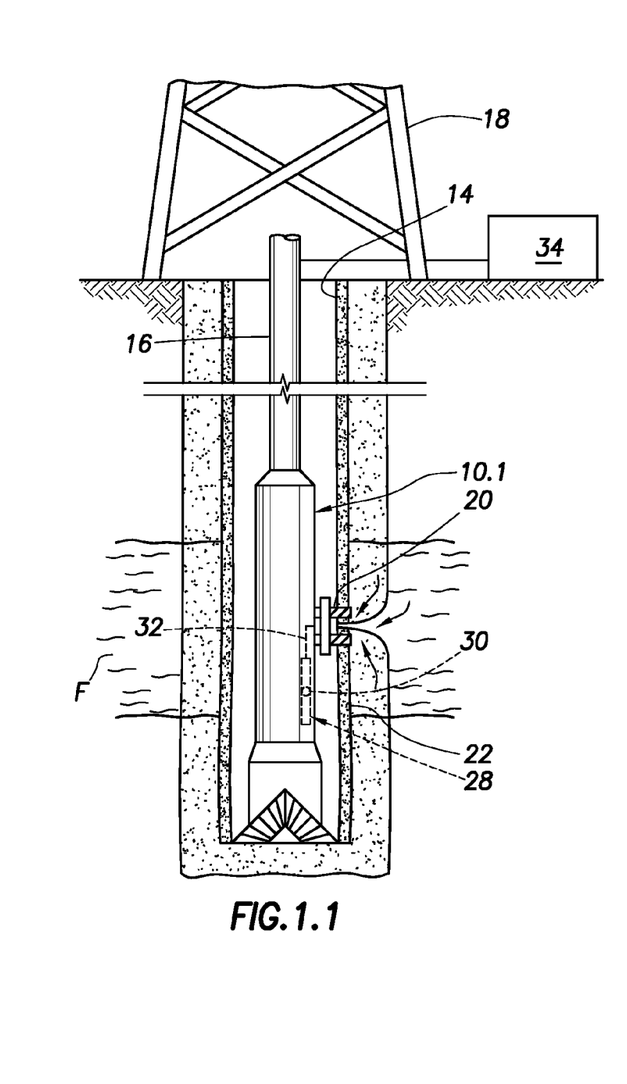
Figure 12:
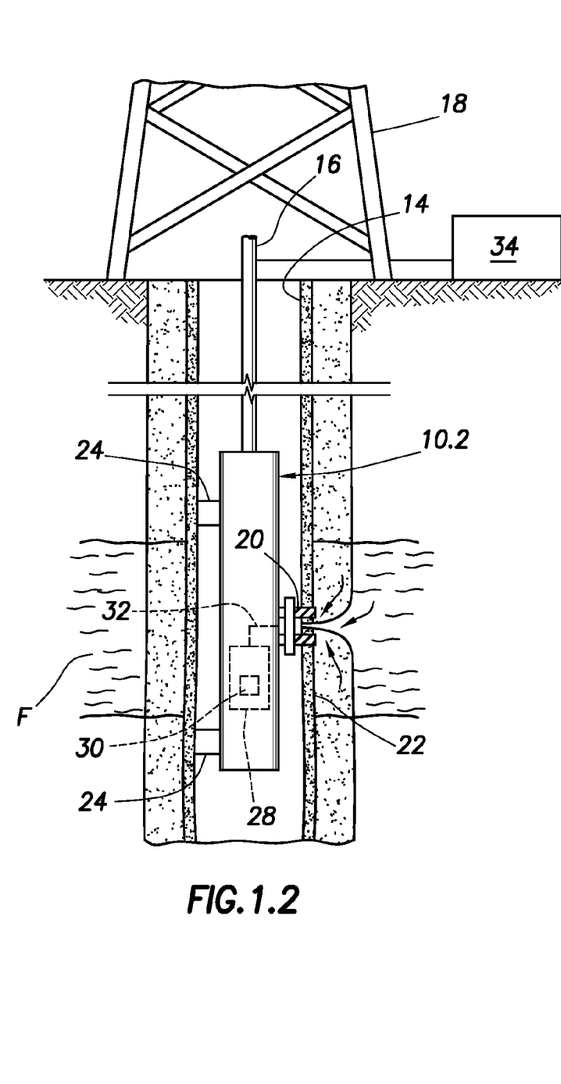

FIGS. 1.1 and 1.2 depict environments in which the subject matter of the present disclosure may be implemented. FIG. 1.1 depicts a downhole drilling tool 10.1 and FIG. 1.2 depicts a downhole wireline tool 10.2 that may be used for performing formation evaluation. The downhole drilling tool 10.1 may be advanced into a subterranean formation F to form a wellbore 14. The downhole drilling tool 10.1 may be conveyed by (or itself may be) a measurement-while-drilling (MWD) drilling tool, a logging-while-drilling (LWD) drilling tool, or other drilling tool(s). The downhole drilling tool 10.1 is attached to a drillstring 16 driven by a rig 18 to form the wellbore 14. The downhole drilling tool 10.1 includes a probe 20 adapted to seal with a wall 22 of the wellbore 14 to draw fluid from the formation F into the downhole drilling tool 10.1 as depicted by the arrows.

The downhole drilling tool 10.1 may be withdrawn from the wellbore 14, and the downhole wireline tool 10.2 of FIG. 1.2 may be deployed from the rig 18 into the wellbore 14 via a wireline cable 16. The downhole wireline tool 10.2 is provided with the probe 20 adapted to seal with the wellbore wall 22 and draw fluid from the formation F into the downhole wireline tool 10.2. Backup pistons 24 may be used to assist in pushing the downhole wireline tool 10.2 and the probe 20 against the wellbore wall 22 and adjacent the formation F.

The downhole tools 10.1, 10.2 may also be provided with a formation evaluation tool 28 with a fluid analyzer 30 for analyzing the formation fluid drawn into the downhole tools 10.1, 10.2. The formation evaluation tool 28 includes a flowline 32 for receiving the formation fluid from the probe 20 and passing the fluid to the fluid analyzer 30 for fluid analysis as will be described more fully herein. A surface control unit 34 may be provided to communicate with the downhole tools 10.1, 10.2 for the passage of signals (e.g., data, power, command, etc.) therebetween.

While FIGS. 1.1 and 1.2 depict specific types of downhole tools 10.1 and 10.2, any downhole tool capable of performing formation evaluation may be used, such as drilling, coiled tubing, wireline or other downhole tools. Also, while FIGS. 1.1 and 1.2 depict the fluid analyzer 30 in a wellbore 14, it will be appreciated that the fluid analyzer 30 may be used at a surface and/or downhole location at the wellsite, and/or at an offsite facility for analyzing the fluid.

By positioning the fluid analyzer 30 in the downhole tool, real-time data may be collected in situ at downhole conditions (e.g., temperatures and pressures where formation evaluation is performed) concerning downhole fluids. Fluids may also be evaluated at surface and/or offsite locations. Fluid samples may also be taken to a surface or offsite location and analyzed in one or more fluid analyzers, such as fluid analyzer 30, at such location(s). Data and test results from various locations may be analyzed and compared.

Figure 2:
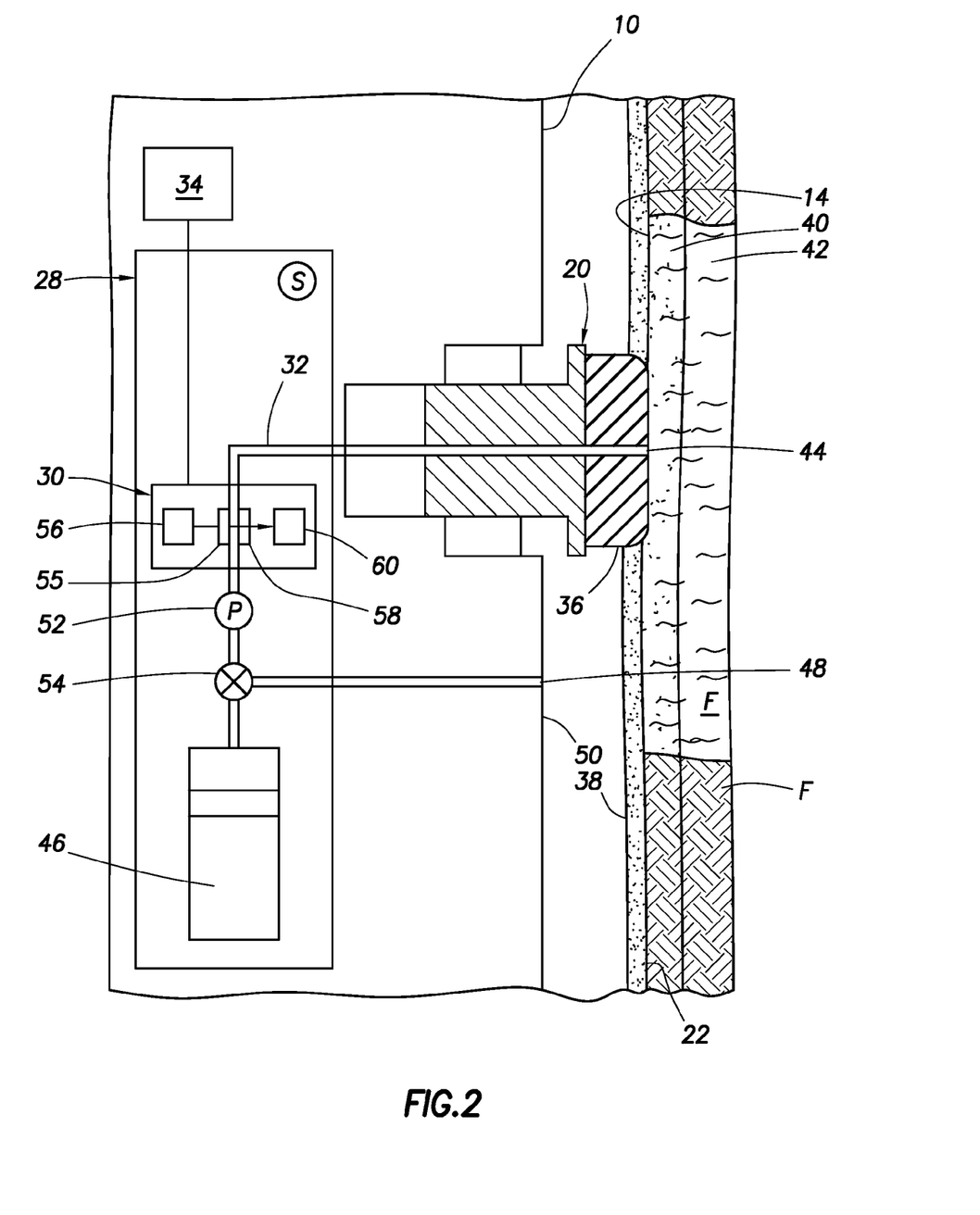
FIG. 2 depicts a schematic view of a portion of a downhole tool having a formation evaluation tool with a fluid analyzer therein in accordance with embodiments of the present disclosure.

FIG. 2 is a schematic view of a portion of a downhole tool 10, which may be either of the downhole tools 10.1 or 10.2 of FIG. 1.1 or 1.2. The probe 20 may be extended from the downhole tool 10 for engagement with the wellbore wall 22. The probe 20 is provided with a packer 36 for sealing with the wellbore wall 22. The packer 36 contacts the wellbore wall 22 and forms a seal with a mudcake 38 lining the wellbore wall 22. A filtrate of the mudcake 38 seeps into the wellbore wall 22 and creates an invaded zone 40 about the wellbore 14. The invaded zone 40 contains the filtrate and other wellbore fluids that may contaminate surrounding formations, such as the formation F, and a portion of clean formation fluid 42 contained therein.

The formation evaluation tool 28 may be provided with one or more flowlines 32 for drawing fluid into the downhole tool 10 through an inlet 44 in the probe 20. While one probe 20 with one inlet 44 is depicted, one or more probes, dual packers and related inlets may be provided to receive downhole fluids and pass them to one or more flowlines 32. Examples of downhole tools and fluid communication devices, are depicted in U.S. Pat. No. 7,458,252, assigned to the assignee of the present disclosure.

The flowline 32 extends into the downhole tool 10 to pass downhole fluid to the formation evaluation tool 28. The formation evaluation tool 28 may be used to analyze, test, sample and/or otherwise evaluate the downhole fluid. A sample chamber 46 is also coupled to the flowline 32 for receiving the downhole fluid. Fluid collected in the sample chamber 46 may be collected therein for retrieval at the surface, or exited through an outlet 48 in housing 50 of the downhole tool 10.

One or more sensors S may optionally be provided to measure various downhole parameters and/or fluid properties. The sensor(s) S may include, for example, gauges, sensors, viscometers, densitometers, gas chromatographs, spectroscopes, analyzers, meters, and/or other devices or detectors capable of taking downhole measurements relating to, for example, downhole conditions and/or fluid properties.

Optionally, flow of the downhole fluid into and/or through the downhole tool 10 may be manipulated by one or more flow control devices, such as a pump 52, the sample chamber 46, valves 54 and/or other devices. Optionally, a downhole control unit 34 may be provided to communicate with the formation evaluation tool 28, the fluid analyzer 30, and/or other portions of the downhole tool 10 for the passage of signals (e.g., data, power, command, etc.) therebetween.

The fluid analyzer 30 is positioned in the formation evaluation tool 28 and coupled to the flowline 32 for receiving the downhole fluid. The fluid analyzer 30 includes a portion of the flowline 32 (and/or additional flowlines fluidly coupled thereto), an optical source 56, an optical window 55, a mirror 58 and an optical sensor (e.g., photodetector) 60.

FIGS. 3.1, 3.2-FIGS. 7.1, 7.2, 7.3 depict various configurations of a fluid analyzer 300-700 which may be used as the fluid analyzer 30 of FIGS. 1.1 and 1.2. In each version, the fluid analyzer 300-700 has various configurations of a flowline 32-32.3 passing fluid therethrough. Each fluid analyzer 300-700 also has various configurations of an optical source 56, an optical window 55, at least one photodetector 60, and at least one mirror 58-58.2 positionable about the flowline 32-32.3 to measure properties of the fluid passing therethrough. The mirror(s) 58-58.2 have an optical layer to selectively permit the passage of light therethrough.

Figure 31:
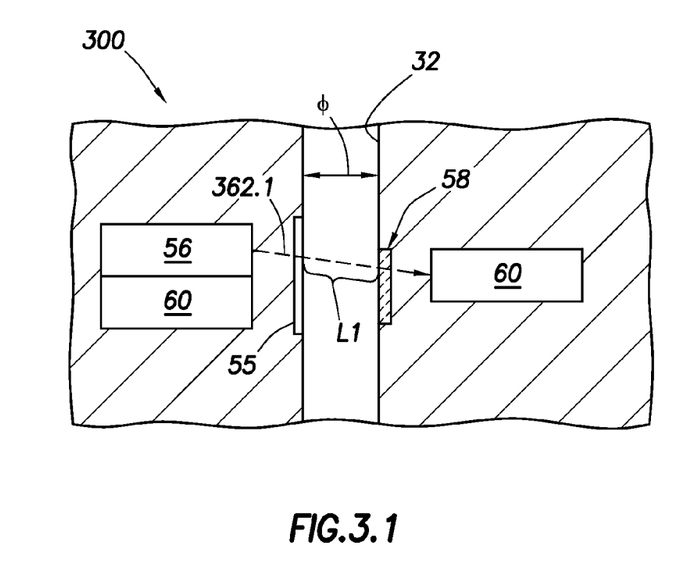
Figure 32:
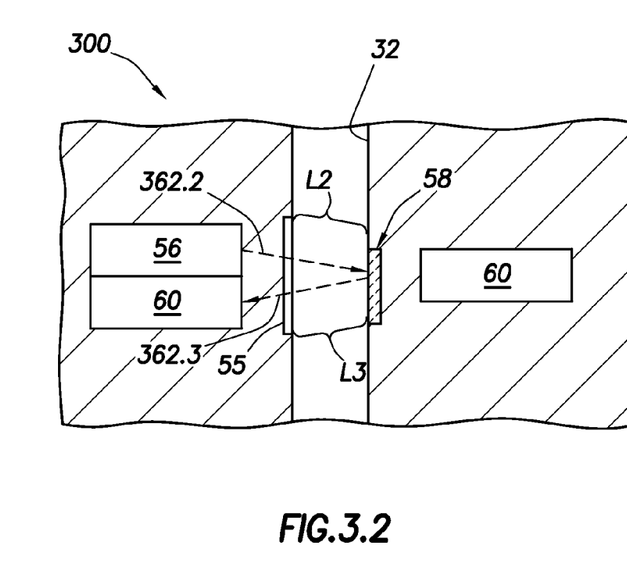
Figure 41:
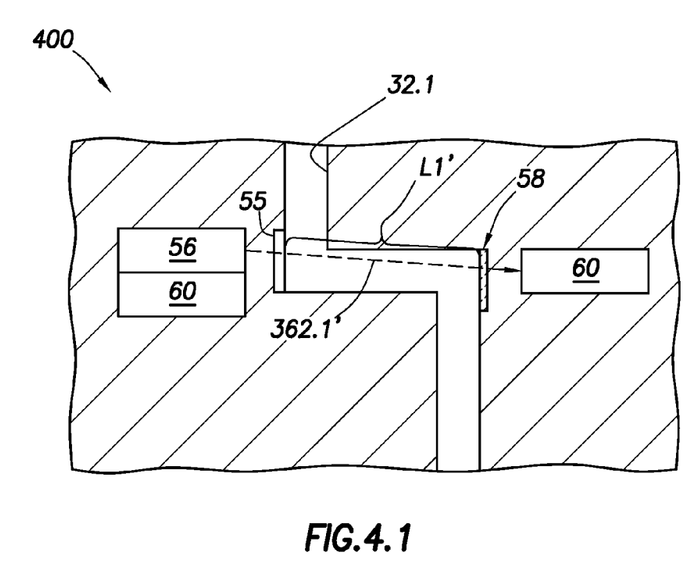
Figure 42:
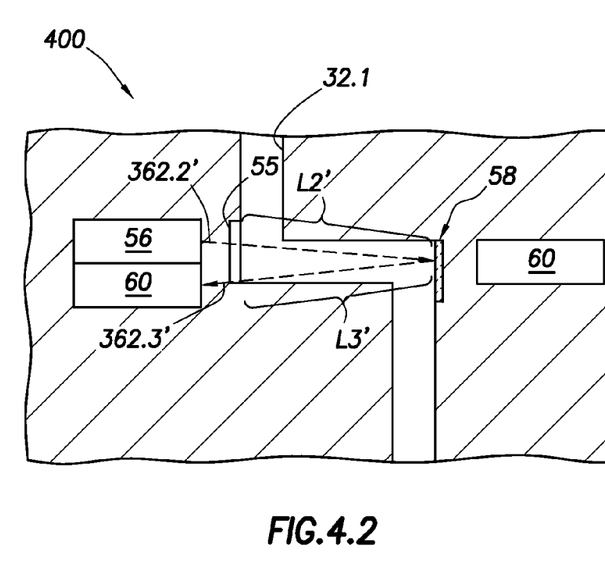
Figure 51:
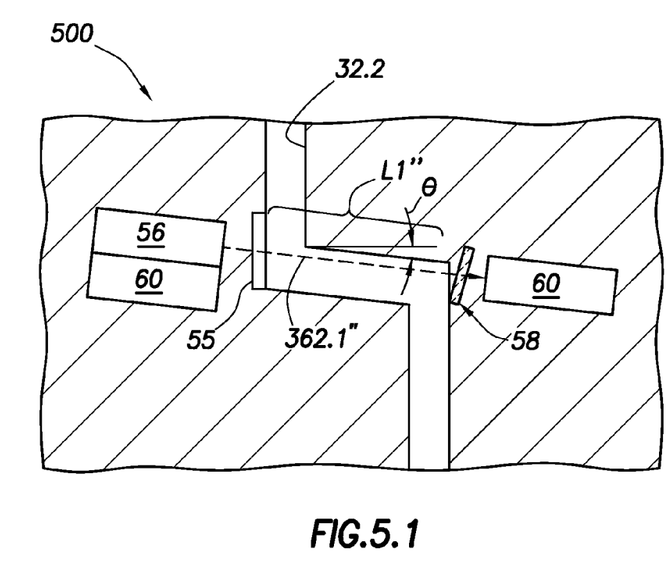
Figure 52:
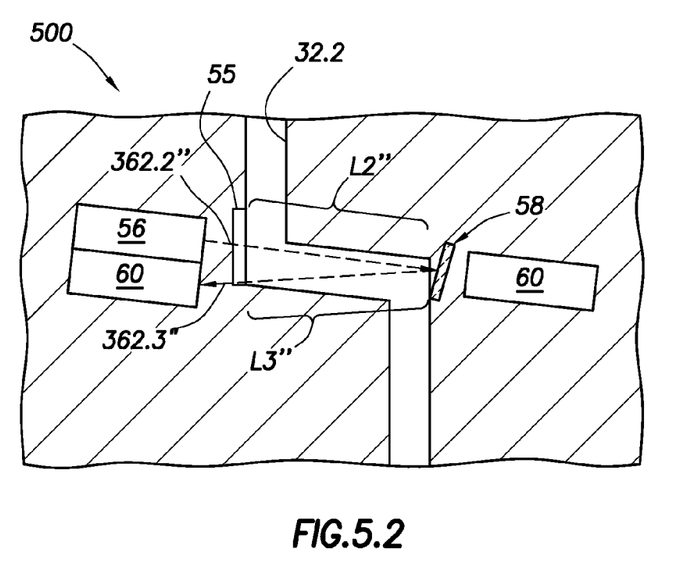

FIGS. 3.1 and 3.2 depict the fluid analyzer 300 in a linear configuration. The flowline 32 is depicted as having a diameter φ for passing fluid therethrough. The diameter φ may be any diameter sufficient for the passage of fluids of various composition or viscosity to pass therethrough in a variety of surface and/or downhole conditions. In an example, the diameter φ may be from about 0.001 mm to about 10 mm.

As also shown in FIGS. 3.1 and 3.2, the flowline 32 is linear and has an active mirror 58 therealong. The optical source 56 is positioned in the fluid analyzer 300 opposite the flowline 32 from the mirror 58 for passing light through the optical window 55 and the fluid passing through flowline 32, and to the mirror 58.

The mirror 58 is an active mirror with an optical layer adjustable (or changeable) between a transmission (or glass) mode as shown in FIG. 3.1 and a reflection (or reflective or mirror) mode as shown in FIG. 3.2. Control unit (surface or downhole) 34 may be used to selectively change modes. In the transmission mode, the mirror 58 permits the light from the optical source 56 to pass through mirror 58 as indicated by dashed line 362.1. A photodetector 60 is positioned adjacent the mirror 58 to receive light from the optical source 56 that passes through the mirror 58.

In reflection mode of FIG. 3.2, light passes along dashed line 362.2 to the mirror 58, and the mirror 58 reflects light from the optical source 56 back through the flowline 32 as indicated by dashed line 362.3. Another photodetector 60 is positioned in the fluid analyzer 300 opposite the mirror 58 to receive light from the optical source 56 that is reflected by the mirror 58.

One or more optical sources 56 may be provided to emit light, such as lasers, through the fluid in flowline 32 and to the mirror 58 for measurement by one or more optical photodetectors 60. The optical sources 56 may be, for example, a lamp (halogen lamp, deuterium lamp, xenon lamp etc), light emitting diode (LED), laser or other light sources passable through the fluid and detectable by a photodetector.

One or more photodetectors 60 may be positioned about the fluid analyzer 300 to receive light passing through or reflected by the mirror 58. The photodetector 60 may be, for example, a photo diode (with or without an optical filter), grating spectrometer, photomultiplier tube (with or without an optical filter), or other sensor capable of measuring optical parameters of fluids from the light received from the optical source 56.

The optical fluid analyzer may have optical sensors, photodetectors, optical sources and other features, such as those of MIFA™ (Modular In situ Fluid Analyzer), LFA™ (Live Fluid Analyzer), LFA-pH™ (Live Fluid Analyzer with pH), OFA™ (Optical Fluid Analyzer), and CFA™ (Composition Fluid Analyzer) commercially available from SCHLUMBERGER TECHNOLOGY CORPORATION™ (see www.sib.com), spectrometers, and/or optical spectroscopy tools capable of measuring optical fluid properties. See also Application Nos. US2011/0061439 and WO2009/009409, previously incorporated by reference herein.

Light passing from optical source 56 to photodetector 60 defines an optical path length L1 extending along line 362.1 from the optical window 55 to the mirror 58. The overall optical path length L of the light in FIG. 3.1 is L1.

"Optical path length" as used herein relates to a length of an interaction volume within the flowline where physical phenomenon can take place. In the example fluid analyzer 300 as shown in FIG. 3.1, the optical path length L1 is defined as the length of between the optical window 55 and the mirror 58 where downhole fluids flows through the flowline 32 and the light from the optical source 56 passes through, and where the optical absorption by downhole fluids may take place. Thus, in FIG. 3.1, the optical path length, L1, extends from a left inner wall of the flowline 32 to a right inner wall of the flowline 32 or from the surface of the optical window 55 to the surface of the mirror 58.

The optical path length of the light passing from the optical window 55 to the mirror 58 along line 362.2 is L2, and the light reflected back from the mirror 58 to the optical window 55 along line 362.3 is L3. The overall optical path length L of the light for FIG. 3.2 is L2+L3. Optical path lengths may be, for example, about 2 mm, or from about 0.001 mm to about 10 mm. As demonstrated by FIGS. 3.1 and 3.2, by altering the mirror between the transmission mode and the reflection mode, the optical path length may be varied.

Figure 8:
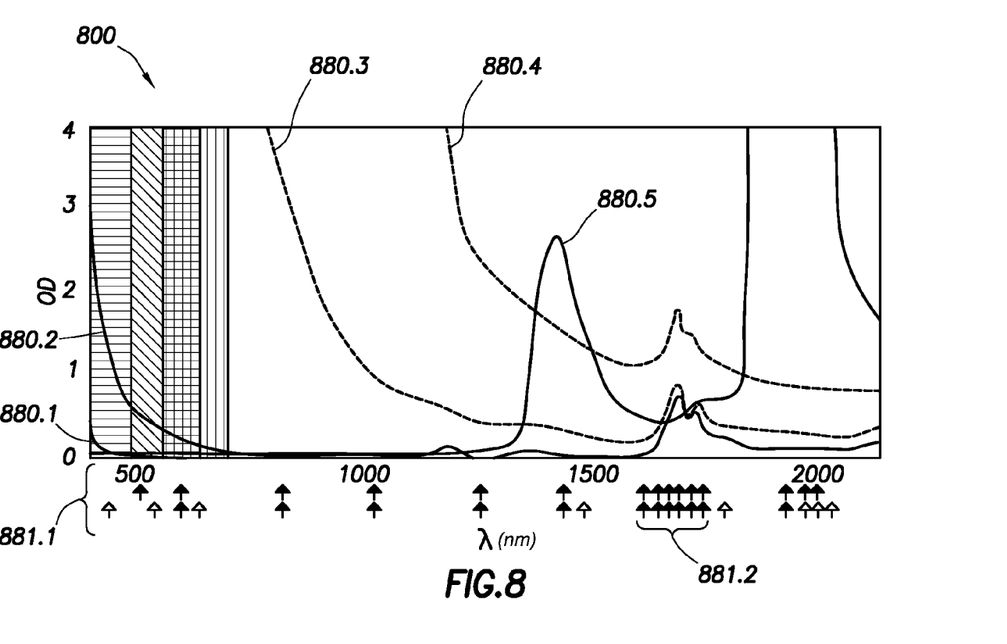
FIG. 8 is a graph depicting an optical scan by a fluid analyzer in accordance with embodiments of the present disclosure.

FIG. 8 is a graph 800 depicting example measurements of fluid taken by an optical sensor, such as the photodetectors 60 herein. The graph 800 plots optical density (y-axis) versus wavelength (λ) (x-axis) of various fluids, such as an oil-based mud (OBM) filtrate 880.1, a condensate 880.2, medium oil 880.3, heavy oil 880.4, and water 880.5. As shown by FIG. 8, various fluids have various optical densities at various wavelengths that are measureable by the photodetectors.

The measurements may be manipulated to enhance output as depicted in graph 800. Measurements of optical density (OD) may range, for example, from about 0 to about 1, to allow an OBM filtrate peak to be seen. In another example, this range may be altered to see a much larger water peak. The optical density range may also be varied, for example, to measure a desired wavelength (e.g., around 1700 nm), to provide an optimal signal-to-noise ratio, and/or to realize high accuracy optical measurements. Signals containing various data may be sent through various channels of the fluid analyzer as shown by inputs 881.1. Additional grating channels may be provided to send additional signals as shown by 881.2.

Hydrocarbon including several type of fluids, such as OBM filtrate, water, and $CO_2$ may be analyzed using a fixed measurement range of optical density (OD) (e.g., from about 0 to about 4). Each substance measured may have different absorption rate, and, therefore, may need to be measured at an optimized range at each substance peak to increase accuracy. One way to change the range is to change optical path length by retrieving the downhole tool and changing mechanical parts. Another way to make desired adjustments may be to selectively adjust the optical path length by altering the mode of the mirror 58 between the transmission and reflection modes as shown in the examples herein.

As shown in FIGS. 3.1 and 3.2, the active mirror 58 may be adjusted between the transmission mode and the reflection mode to achieve the desired optical path length and the desired optical density (OD). The mode may be changed, for example, using the control unit 34 by altering a few voltages of electric power to the fluid analyzer 30. Increased variable optical density may allow for measurement of fluids, such as $H_2S$, with absorption rates that may be outside of a range of other desired fluids, such as hydrocarbons.

FIGS. 4.1-5.2 show additional examples of flowline configurations that may be used, and modes of active mirrors that are altered to vary optical path length. Referring first to FIGS. 4.1 and 4.2, an optical analyzer 400 in a bent configuration is depicted. The optical analyzer 400 of FIGS. 4.1 and 4.2 is the same as the optical analyzer 300 of FIGS. 3.1 and 3.2, respectively, except that a bent flowline 32.1 is provided. In this version, the bent flowline 32.1 is bent at a right angle to provide a horizontal path for passing the light from the optical source 56 to the mirror 58. The optical path lengths L1', L2' and L3' are generated along lines 362.1', 362.2', and 362.3', respectively. FIG. 4.1 has an optical path length L=L1'. FIG. 4.2 has an optical path length L=L2'+L3'.

Referring now to FIGS. 5.1 and 5.2, an optical analyzer 500 in an angular configuration is depicted. The angular configuration of FIGS. 5.1 and 5.2 is the same as the bent configuration of FIGS. 4.1 and 4.2, respectively, except that an angular flowline 32.2 is bent at an angle θ and the mirror 58 is tilted. The optical path lengths L1", L2" and L3" are generated along lines 362.1", 362.2", or 362.3", respectively. FIG. 5.1 has an optical path length L=L1". FIG. 5.2 has an optical path length L=L2"+L3".

Figure 61:
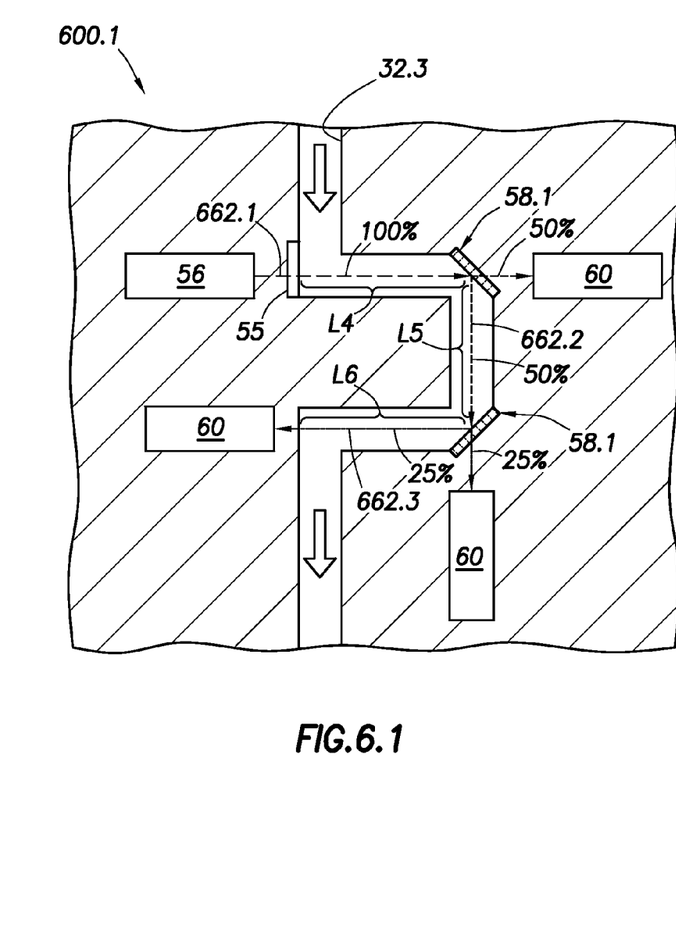
Figure 62:
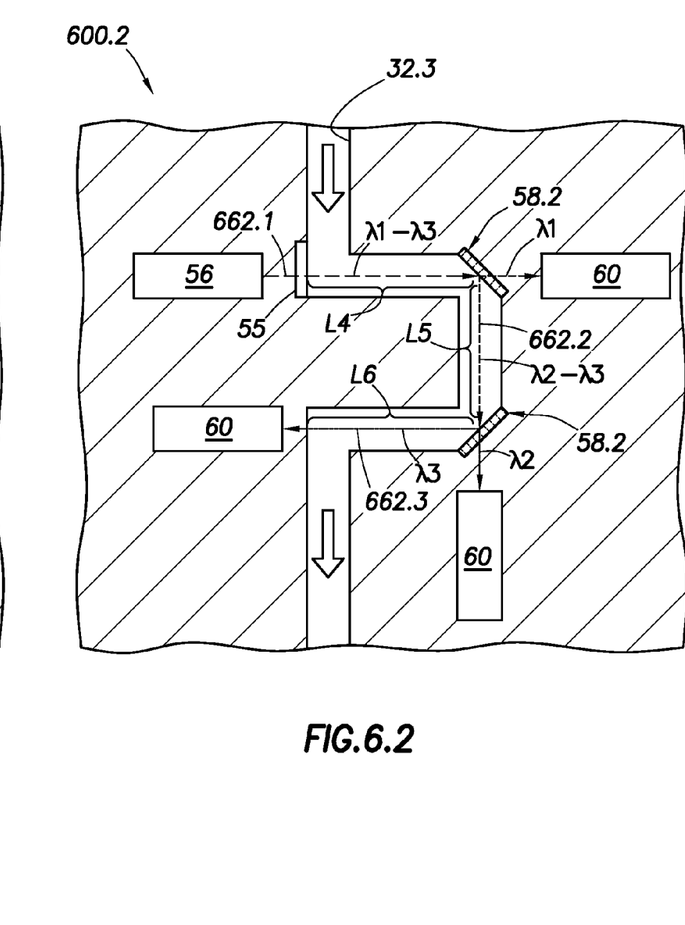
Figure 71:
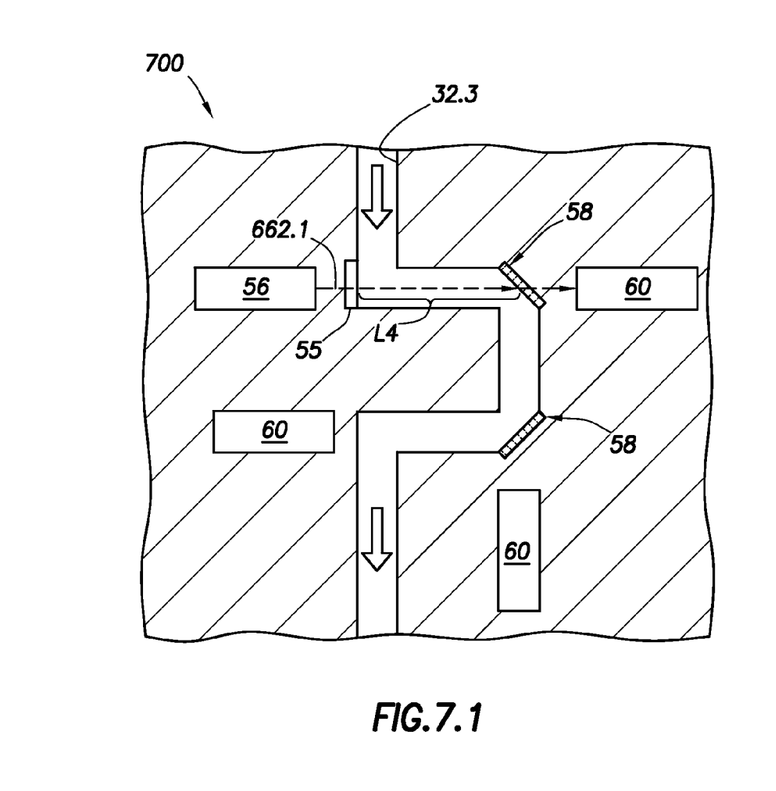
Figure 72:
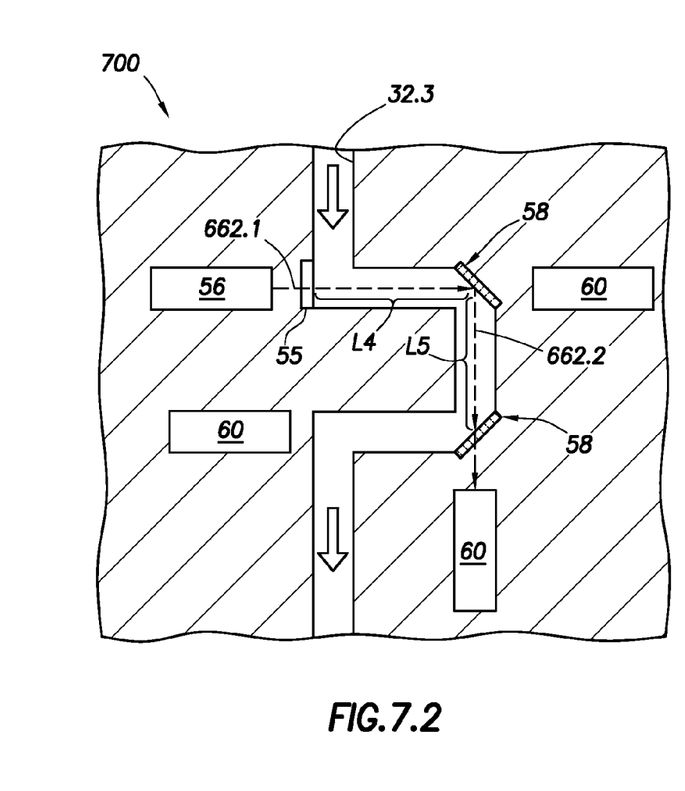
Figure 73:
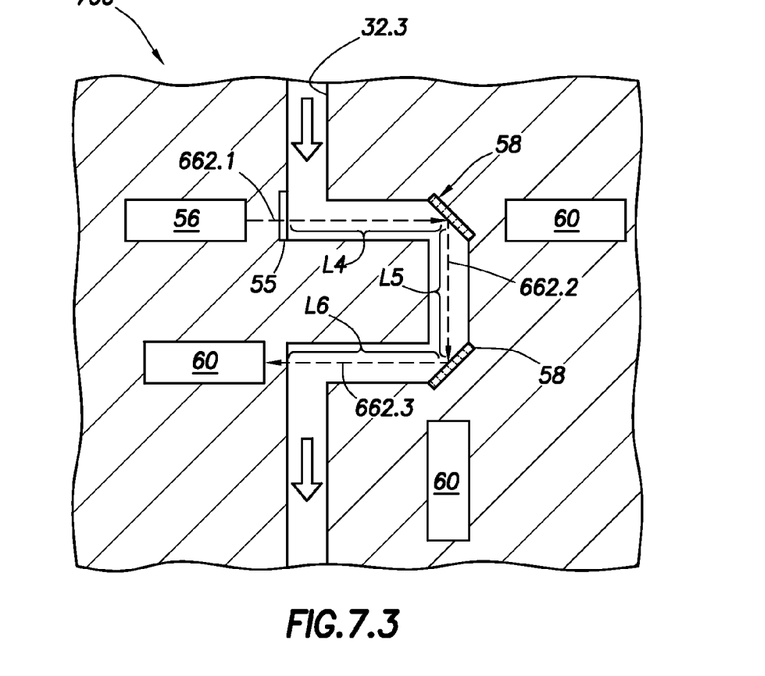

FIGS. 6.1 and 6.2 show additional examples of passive mirrors and multi-bent flowline configurations that may be used. Passive mirrors may have an optical layer to permit a portion of light to pass therethrough and may not require activation by control unit 34. FIGS. 6.1 and 6.2 depict optical analyzers 600.1, 600.2 which include a flowline 32.3 with a plurality of bends therealong. As shown in FIGS. 6.1 and 6.2, a first mirror 58.1, 58.2 is positioned at a first bend, and a second mirror 58.1, 58.2 is positioned at a second bend along the flowline 32.3. As demonstrated by the various configurations, one or more bends may be provided along the flowline, and mirrors, optical sources and photodetectors positioned therealong to take measurements as desired.

The optical analyzers 600.1, 600.2 of FIGS. 6.1 and 6.2 are similar to the optical analyzer 400 of FIGS. 4.1 and 4.2, except that flowline 32.3 is provided with multiple bends with multiple mirrors 58.1, 58.2 and multiple photodetectors 60 therealong, and that the mirrors 58.1 and 58.2 are passive mirrors. As shown by these configurations, the optical source 56 passes light along line 662.1 to a first mirror 58.1, 58.2. Light is emitted from the optical source 56 to the first mirror 58.1, 58.2 along a first portion of the flowline 32.3 and defines an optical path length L4 therealong.

Light reflected from the first mirror 58.1, 58.2 to a second mirror 58.1, 58.2 travels along line 662.2 in a second portion of the flowline 32.3 and defines an optical path length L5 therealong. Light reflects from the second mirror 58.1, 58.2 to a photodetector 60 along line 662.3 in a third portion of the flowline 32.3 and defines an optical path length L6 therealong. The overall optical path length may be varied from L4, to L4+L5, to L4+L5+L6, and the desired optical path length selected therefrom.

The optical analyzer 600.1 of FIG. 6.1 has a beam splitter (or partial) mirror 58.1 which permits passage of a percentage of the light 662.1 therethrough, and reflects a percentage of the light 662.2 to the next mirror 58.1. In an example, the beam splitter mirror 58.1 may allow 50% of the light to pass therethrough and 50% of the light to be reflected. The next beam splitter mirror 58.1 may also reflect half of the light received, and allows half of the light received to pass therethrough. In an example, 50% of the light is received by the second mirror 58.1 along line 662.2. Half of the light received by second mirror 58.1 (or 25% total) passes therethrough for measurement by a second photodetector 60, and half (or 25% total) is reflected on to a third photodetector 60 along line 662.3.

The optical analyzer 600.2 of FIG. 6.2 has a wavelength selective (or specific) mirror 58.2 which selectively permits passage of the light 662.1 therethrough, and selectively reflects the light 662.2 to the next mirror 58.2. The wavelength selective mirror 58.2 may selectively permit a portion of the light at certain wavelengths therethrough. Wavelength selective mirrors may be used to transmit or reflect the light at a certain wavelength with a band width of the order of about 10 nm to about 20 nm or less. For example, a wavelength selective mirror may be a dichroic mirrors, band pass filters, laser line mirrors, and the like.

In an example, optical source 56 passes light having wavelengths 21-23 along the line 662.1 to wavelength selective mirror 58.2 which allows λ1 to pass therethrough and wavelengths λ2-λ3 to be reflected. The next wavelength specific mirror 58.2 may allow wavelength λ2 to pass therethrough for measurement by a second photodetector 60, but may reflect wavelength λ3 on to a third photodetector 60 for measurement. The wavelengths reflected or passed through the mirrors 58.2 may be selected as desired.

FIGS. 7.1-7.3 show an example sequence of fluid analysis using the fluid analyzer 700 in a bent configuration with active mirrors 58. The fluid analyzer 700 includes the flowline 32.3 with optical source 56, photodetectors 60, and active mirrors 58. As shown in FIG. 7.1, light is passed from the optical source 56 along line 662.1 to active mirror 58 and passes in transmission mode therethrough for measurement by photodetector 60. Mirror 58 is then changed to reflection mode, and light is then reflected from mirror 58 along line 662.2 to active mirror 58 as shown in FIG. 7.2. Active mirror 58 is initially in transmission mode to pass the light therethrough for measurement by photodetector 60. Active mirror 58 then changes to reflection mode and reflects light along line 662.3 for measurement by photodetector 60 as shown in FIG. 7.3. As in FIGS. 6.1 and 6.2, the overall optical path length may be varied from L4, to L4+L5, to L4+L5+L6, and the desired optical path length selected therefrom.

While FIGS. 3.1 through 7.3 depict various configurations of flowlines, optical sources, photodetectors and mirrors, it will be appreciated that various combinations of these items may be provided. For example, a variety of mirrors and/or flowline configurations may be used to facilitate measurements in the fluid analyzer. The mirrors may provide selective reflection and/or passage therethrough for measurement along a flowline as desired. One or more such passive (e.g., percentage, half, wavelength) mirrors and/or active mirrors may be provided. Examples of passive mirrors that may be used are commercially available from SIGMA KOKI™ at http://www.sigma-koki.com. Examples of active mirrors that may be used are described, for example, by THE NATIONAL INSTITUTE OF ADVANCED INDUSTRIAL SCIENCE AND TECHNOLOGY™ (AIST), see: http://www.aist.go.jp.

The passive and active mirrors may be selected for use in the fluid analyzer along various portions thereof. The selected mirror(s) may provide for the passage of selective portions of the light to selective photodetectors for measurements thereby. The light may be selectively (passively and/or actively) diverted to one or more mirrors and/or one or more photodetectors for measurements thereof. Portions of the light passing through the fluid may be selected to pass to a photodetector to allow measurement(s) thereof. Such selective measurement(s) may be used, for example, to provide similar wavelengths to certain photodetectors, thereby permitting a more focused range of measurements thereof.

Figure 9:
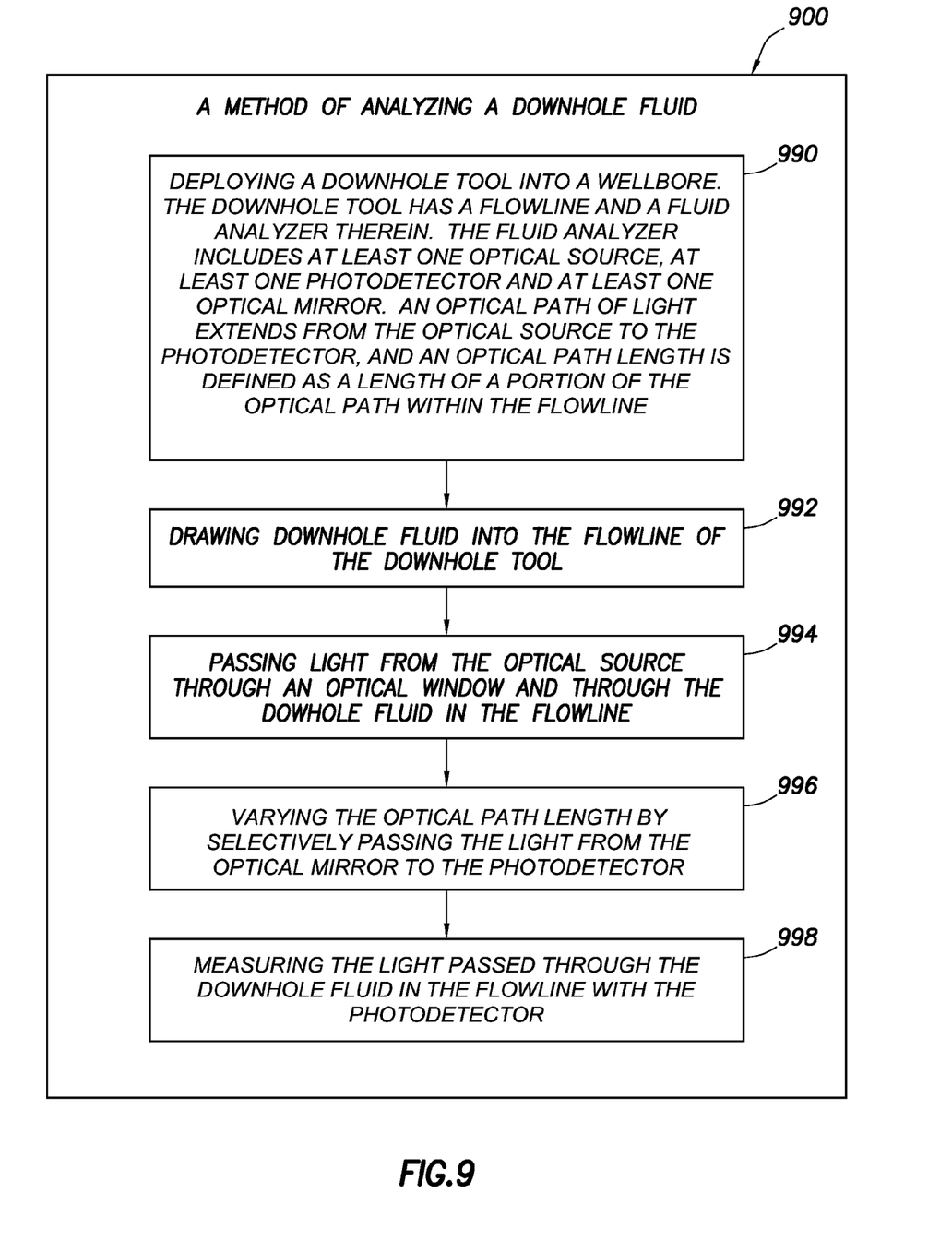
FIG. 9 is a flow chart depicting a method of analyzing a downhole fluid in accordance with embodiments of the present disclosure.

FIG. 9 shows a flow chart 900 of a method of analyzing a downhole fluid. The method 900 involves deploying (990) a downhole tool into a wellbore. The downhole tool has a flowline and a fluid analyzer therein. The fluid analyzer includes at least one optical source, at least one photodetector and at least one optical mirror. An optical path of light extends from the optical source to the photodetector. An optical path length is defined as a length of a portion of the optical path within the flowline. The method also involves drawing (992) downhole fluid into the flowline of the downhole tool, passing light (994) from the optical source through an optical window and through the downhole fluid in the flowline, varying (996) the optical path length by selectively passing the light from the optical mirror to the photodetector, and measuring (998) the light passed through the downhole fluid in the flowline with the photodetector.

The method may involve using a passive mirror to pass portions of the light through the passive mirror and to the photodetector for measurement thereby, and/or using an active mirror to selectively pass the light through the active mirror or reflect the light from the active mirror to the photodetector for measurement thereby. The method may involve passing the light from a photodetector to a mirror, and selectively passing the light from a first mirror to one or more additional mirrors and on to at least one more photodetector. At least a portion of the light may pass through the mirror and/or be reflected thereby.

The collected measurements may be analyzed. The analysis may involve evaluation using measurements from the sensor(s) S or other known data. Measurements at various optical path lengths may be compared and/or evaluated. The method may be performed in any order and repeated as desired.

Plural instances may be provided for components, operations or structures described herein as a single instance. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A fluid analyzer of a downhole tool positionable in a wellbore penetrating a subterranean formation, the wellbore having a downhole fluid thereabout, the downhole tool having a housing with a flowline therethrough for receiving the downhole fluid, the fluid analyzer comprising:
   at least one optical source to pass a light through an optical window and through the downhole fluid in the flowline;
   at least one photodetector to measure the light passed through the downhole fluid in the flowline, an optical path of the light extending from the at least one optical source to the at least one photodetector, an optical path length defined as a length of a portion of the optical path within the flowline; and
   at least one optical mirror positionable about the flowline, the at least one optical mirror having an optical layer selectively passing the light from the at least one optical mirror to the at least one photodetector whereby the optical path length may be varied.

2. The fluid analyzer of claim 1, wherein the at least one optical mirror comprises a passive mirror selectively permitting a portion of the light therethrough.

3. The fluid analyzer of claim 2, wherein the passive mirror is one of a wavelength selective mirror and a beam splitter mirror.

4. The fluid analyzer of claim 1, wherein the at least one optical mirror comprises an active mirror adjustable between a transmission mode permitting light therethrough and a reflection mode reflecting light therefrom.

5. The fluid analyzer of claim 1, wherein the optical layer selectively restricts at least a portion of the light from passing therethrough.

6. The fluid analyzer of claim 1, wherein the optical layer selectively reflects at least a portion of the light from the at least one optical mirror and to the at least one photodetector.

7. The fluid analyzer of claim 1, wherein the optical layer selectively passes at least a portion of the light through the at least one optical mirror and to the at least one photodetector.

8. The fluid analyzer of claim 1, wherein the optical path extends from the optical window through the at least one optical mirror and to the at least one photodetector.

9. The fluid analyzer of claim 1, wherein the optical path length extends from the optical window to the at least one optical mirror and from the at least one optical mirror back through the flowline to the at least one photodetector.

10. The fluid analyzer of claim 1, wherein the optical path length extends from the optical window to the at least one optical mirror and from the at least one optical mirror to at least one additional optical mirror and to the at least one photodetector.

11. The fluid analyzer of claim 1, wherein the flowline is one of linear, bent, angular, multi-bent and combinations thereof.

12. The fluid analyzer of claim 1, wherein the flowline has a plurality of bends and a plurality of optical mirrors, each of the plurality of optical mirrors positioned at each of the plurality of bends.

13. The fluid analyzer of claim 1, wherein the at least one photodetector is positioned at one of an opposite side and a same side the flowline from the at least one optical mirror.

14. A downhole tool positionable in a wellbore penetrating a subterranean formation, the wellbore having a downhole fluid thereabout, the downhole tool comprising:
- a housing having a flowline extending therethrough to receive the downhole fluid; and
- a fluid analyzer comprising:
    - at least one optical source to pass a light through an optical window and through the downhole fluid in the flowline;
    - at least one photodetector to measure the light passed through the downhole fluid in the flowline, an optical path of the light extending from the at least one optical source to the at least one photodetector, an optical path length defined as a length of a portion of the optical path within the flowline; and
    - at least one optical mirror positionable about the flowline, the at least one optical mirror having an optical layer to selectively pass the light from the at least one optical mirror to the at least one photodetector whereby the optical path length may be varied.

15. The downhole tool of claim 14, further comprising a control unit to selectively activate the at least one optical mirror.

16. A method of measuring fluid of a wellbore penetrating a subterranean formation, comprising:
- deploying a downhole tool into the wellbore, the downhole tool having a flowline and a fluid analyzer therein, the fluid analyzer comprising at least one optical source, at least one photodetector and at least one optical minor, an optical path of the light extending from the at least one optical source to the at least one photodetector, an optical path length defined as a length of a portion of the optical path within the flowline;
- drawing downhole fluid into the flowline of the downhole tool;
- passing light from the at least one optical source through an optical window and through the downhole fluid in the flowline;
- varying the optical path length by selectively passing the light from the at least one optical mirror to the at least one photodetector; and
- measuring the light passed through the downhole fluid in the flowline with the at least one photodetector.

17. The method of claim 16, wherein varying the optical path length comprises passing select wavelengths of the light through the at least one optical mirror.

18. The method of claim 16, wherein varying the optical path length comprises passing a percentage of the light through the at least one optical mirror.

19. The method of claim 16, wherein varying the optical path length comprises reflecting at least a portion of the light from the at least one mirror.

20. The method of claim 16, wherein varying the optical path length comprises selectively shifting the at least one optical mirror between a transmission mode passing the light through the at least one optical mirror and a reflection mode reflecting the light from the at least one optical mirror.

* * * * *